(12) United States Patent
Camp

(10) Patent No.: US 6,846,318 B2
(45) Date of Patent: *Jan. 25, 2005

(54) SCLERAL PLUG SYSTEM

(76) Inventor: Matthew W. Camp, 4065 Hickory Fairway Dr., Woodstock, GA (US) 30188-2343

( * ) Notice: Subject to any disclaimer, the term of this patent is extended or adjusted under 35 U.S.C. 154(b) by 0 days.

This patent is subject to a terminal disclaimer.

(21) Appl. No.: 10/441,337

(22) Filed: May 20, 2003

(65) Prior Publication Data

US 2003/0208216 A1 Nov. 6, 2003

Related U.S. Application Data

(63) Continuation of application No. 09/658,287, filed on Sep. 8, 2000, now Pat. No. 6,706,275.
(60) Provisional application No. 60/152,839, filed on Sep. 8, 1999.

(51) Int. Cl.$^7$ .............................................. A61B 17/50
(52) U.S. Cl. ...................................................... 606/210
(58) Field of Search ................................ 606/205, 207, 606/210, 211, 108, 213, 107; 424/400, 422

(56) References Cited

U.S. PATENT DOCUMENTS

| | | | | |
|---|---|---|---|---|
| 4,764,170 A | * | 8/1988 | Drews ........................ | 606/107 |
| 4,844,065 A | | 7/1989 | Faulkner | |
| 4,955,896 A | * | 9/1990 | Freeman ..................... | 606/210 |
| 5,283,063 A | * | 2/1994 | Freeman ..................... | 606/107 |
| 5,423,777 A | * | 6/1995 | Tajiri et al. ................. | 606/107 |
| 5,626,559 A | | 5/1997 | Solomon | |
| 5,707,643 A | | 1/1998 | Ogura et al. | |
| 6,234,175 B1 | * | 5/2001 | Zhou et al. ................. | 128/887 |
| 6,238,363 B1 | * | 5/2001 | Kurihashi ................... | 606/107 |
| 6,428,502 B1 | * | 8/2002 | Lang .......................... | 604/28 |
| 6,605,108 B2 | * | 8/2003 | Mendius et al. ........... | 623/1.11 |
| 6,706,275 B1 | * | 3/2004 | Camp ......................... | 606/108 |

* cited by examiner

*Primary Examiner*—David O. Reip
*Assistant Examiner*—Jessica R. Baxter
(74) *Attorney, Agent, or Firm*—Camilla C. Williams; Kilpatrick Stockton LLP

(57) ABSTRACT

Scleral plug system for occluding a hole in the eye and for controlling irrigation during vitreo-retinal surgery in order to maintain a closed system during the procedure, and angled forceps for handling a scleral plug.

3 Claims, 2 Drawing Sheets

SCLERAL PLUG SYSTEM

This application is a continuation application of U.S. Ser. No. 09/658,287 filed on Sep. 8, 2000, now U.S. Pat. No. 6,706,275, which claims the benefit of U.S. Provisional Application No. 60/152,839 filed on Sep. 8, 1999, the entire contents of which are incorporated herein by reference.

BACKGROUND OF THE INVENTION

1. Field of the Invention

This invention relates to a scleral plug for occluding a hole in the eye and for controlled irrigation during vitreo-retinal surgery in order to maintain a closed system during the procedure, and angled forceps for handling the plugs.

2. Description of Related Art

Modern vitreo-retinal surgery allows ophthalmologists to diagnose and treat diseases of and injuries to the posterior segment of the eye. Vitreo-retinal surgery involves the use of small needle instruments to remove, for example, the vitreous humor, hemorrhage, scar tissue, infection or foreign bodies.

A typical three port vitrectomy utilizes an infusion cannula, which maintains a preset tension in the eye, and multiple hand-held instruments for illumination, cutting, grasping, and suction. A carefully constructed environment must be maintained within the eye at all times for these procedures to be successful. The surgeon uses microsurgical techniques to manipulate the delicate tissue within the eye. The instruments are introduced into the vitreous cavity through sclerotomies, or small holes, in the area of the pars plana ciliaris.

Small steel plugs are utilized during vitreo-retinal surgery to occlude the sclerotomy sites when instruments are not inserted through these access holes in the sclera. The plugs of the prior art have a straight shaft and a cap on one end. Inserting these plugs into the access holes allows the surgeon to maintain a closed system, which is important for the prevention of pressure loss, egress of fluid or globe contents, and entrance of bacteria or debris. These access holes, or sclerotomies, are manipulated by repeated passing of instruments and will tend to stretch and enlarge, allowing the plugs to slip out. There is a need for a scleral plug that will remain in place during vitreo-retinal surgery, allowing a surgeon to maintain a closed system.

Proliferative vitreoretinopathy (PVR) is the leading cause of failure of retinal detachment repair. Although the etiology is somewhat controversial, one theory implicates the retinal pigment epithelial (RPE) cells. RPE cells are "workhorse" type cells with fibroblastic, or scar forming, potential. During formation of retinal tears or treatment with cryotherapy, these RPE cells may be released into the vitreous cavity, increasing the chances of PVR. Currently, during a vitrectomy, the surgeon can irrigate these cells from the eye using a flute needle, called a Charles Needle. This type of irrigation requires the surgeon to manually hold instruments in the eye for 30–60 seconds or more. Thus, there is a need for a plug that would allow controlled egress of fluid without requiring the surgeon's strict attention and active manipulation.

Forceps used in the art to manipulate scleral plugs are currently reverse acting—they grip until you squeeze to release. Thus, the instrument will hold a plug until placed and released by the surgeon. Current forceps have a long, angled tip. The length of the tip, combined with the size of the tiny plug, makes it difficult to place a plug in a sclerotomy. Thus, there is a need for forceps that allow easier placement and more exacting control over placement of plugs.

SUMMARY OF THE INVENTION

One embodiment of this invention is a scleral plug with a bulbous, rather than straight, shaft. This plug remains firmly in position during vitreo-retinal surgery and minimizes the likelihood that the plug will slip out of position. In order to maintain a watertight fit while taking care not to stretch the sclerotomy, the proximal end of the shaft has a smaller diameter than the distal bulbous tip. The portion of the shaft having a smaller diameter is of a length to accommodate the thickness of the sclera.

A further embodiment of this invention relates to a plug that functions as a small bore cannula. This plug has a shaft lengthened to about 6 mm and a lumen with an opening through the cap of the plug. Fluid flows into the eye through the infusion cannula until the eye reaches a predetermined pressure. When using the plugs of the prior art, any breach in the system allows fluid to escape uncontrolled, e.g. a leak or an unplugged sclerotomy. A plug with a lumen according to this embodiment allows the surgeon to control the breach in the system. In particular, the surgeon may irrigate the intraocular cavity to remove RPE cells while still maintaining a controlled environment. These RPE cells initially may be released from their sub-retinal location as a result of trauma or retinal breaks. The release of RPE cells are believed to cause PVR, which results in loss of vision. It is important to irrigate the eye so that the RPE cells are expelled from the vitreous cavity. Replacing a standard plug with this cannulated plug, or adding a lumen to the bulbous plug of this invention, allows controlled irrigation of fluid from the eye. If immediate cessation of the irrigation is needed, it can be accomplished simply by placing a finger over the external opening of the lumen.

Fluid turbulence may cause even healthy retina to be drawn toward a sclerotomy and damaged. It is important that retina is not expelled from the intraocular cavity through the sclerotomy site. The cannulated plug of this invention avoids expulsion of the retina. The length of the shaft of this cannulated plug locates the opening of the lumen more centrally within the vitreous cavity and far enough to avoid disturbing the retina.

The forceps of this invention have a shortened tip for ease in handling the minute plugs utilized in vitreo-retinal surgery, while maintaining the overall length of the handles and their reverse-action grip.

Accordingly, it is an object of this invention to provide a scleral plug with a bulbous tip so that the plug remains in position during vitreo-retinal surgery.

It is a further object of this invention to provide a cannulated plug for controlled irrigation during vitreo-retinal surgery.

It is a further object of this invention to provide a cannulated plug that avoids expulsion of the retina.

It is another object of this invention to provide forceps with shortened tips for ease in handling scleral plugs.

DETAILED DESCRIPTION OF SPECIFIC EMBODIMENTS

Figure 1:
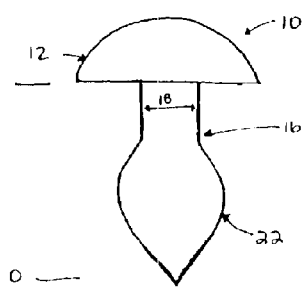
FIG. 1 is a side view of a bulbous scleral plug of this invention.

As shown in FIG. 1, scleral plug 10 has cap 12 at proximal end 14. Shaft 16 is attached to cap 12 at proximal end 14. Proximal end 14 of shaft 16 has diameter 18 that is equivalent to the diameter of the sclerotomy. Distal end 20 has bulbous portion 22. When placed in an eye during surgery, distal end 20 is first placed into the sclerotomy, or opening in the sclera. Bulbous portion 22 passes through the sclera to the interior portion of the eye. Reduced diameter proximal end 14 forms a watertight seal with the sclera. Reduced diameter proximal end 14 has a diameter so that it does not stretch the sclerotomy and is of a length to accommodate the thickness of the sclera. Cap 12 prevents plug 10 from slipping into the eye, while bulbous end 22 prevents plug 10 from slipping out of the eye and thereby disrupting the desired closed system.

Figure 3A:
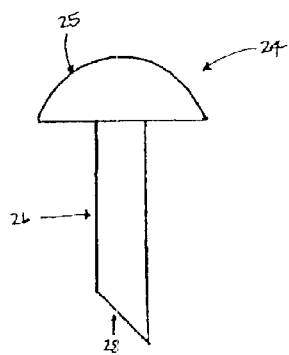
FIG. 3A is a side view of the cannulated plug of this invention.
Figure 3B:
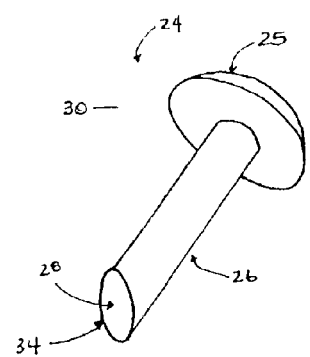
FIG. 3B is a perspective view of the cannulated plug of this invention.
Figure 3C:
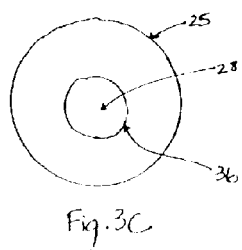
FIG. 3C is a top plan view of the cannulated plug of this invention.
Figure 2:
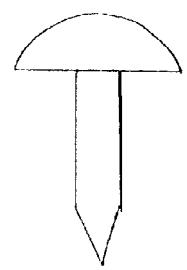
FIG. 2 is a side view of a scleral plug of the prior art.

As shown in FIGS. 3A–3C, cannulated scleral plug 24 has cap 25, shaft 26 and lumen 28. Cap 25 is attached at proximal end 30. Lumen 28 has distal opening 34 and proximal opening 36. Shaft 26 is inserted into the sclerotomy. Lumen 28 allows controlled irrigation of fluid from the eye. This controlled irrigation allows the surgeon to irrigate the intraocular cavity to remove RPE cells while maintaining a controlled environment. Shaft 26 maintains the sclerotomy in an open position and the extended length of shaft 26 protects against expulsion of retina. Distal opening 34 of lumen 28 is located more centrally within the vitreous cavity and far enough within that cavity to avoid disturbing the retina.

Figure 4:
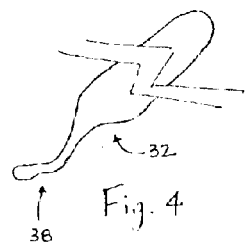
FIG. 4 is a side view of the forceps of this invention.

FIG. 4 shows forceps 32 having shortened tip 38. Tip 38 is angled up from groove 40 (not shown), which is on the inside face of tip 38 of forceps 32. This shortened, angled tip 38 allows easier placement and more exacting control over placement of the plugs.

Figure 6:
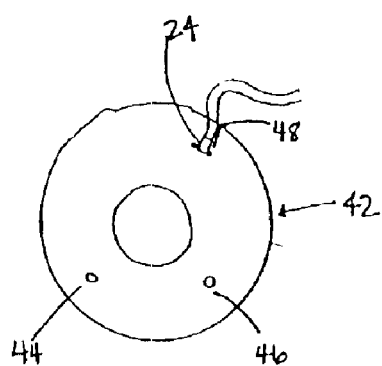
FIG. 6 is a cross-sectional view of a portion of an eye, with the cannulated plug of FIG. 3A in place in a sclerotomy site.
Figure 5:
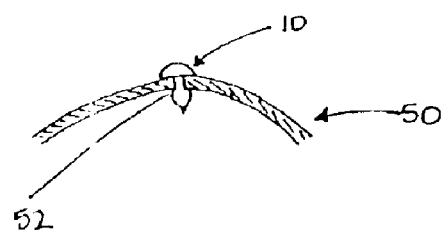
FIG. 5 is a cross-sectional view of a portion of an eye, with the scleral plug of FIG. 1 in place in a sclerotomy site.
Figure 1:
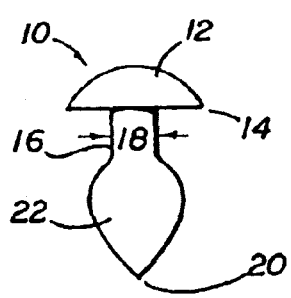
Figure 2:
Figure 3A:
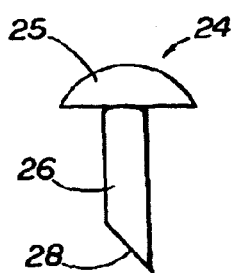
Figure 3B:
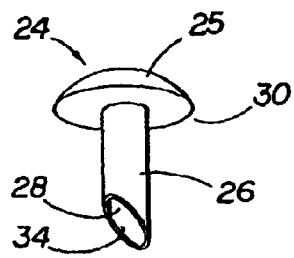
Figure 3C:
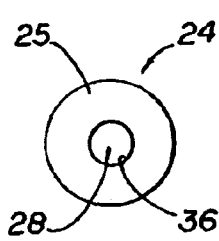
Figure 4:
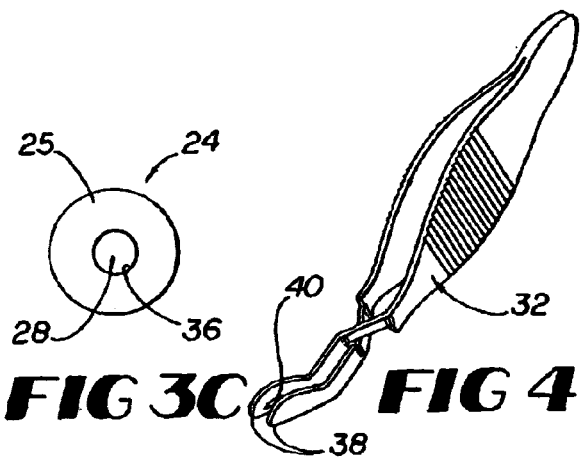
Figure 5:
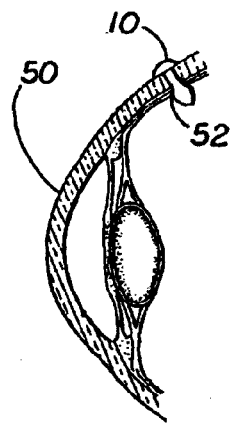
Figure 6:
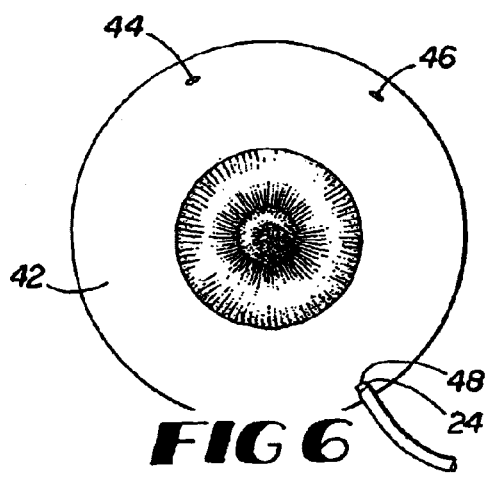

FIG. 5 is a cross-sectional view of a portion of an eye 50 with bulbous scleral plug 10 in position in sclerotomy site 52. FIG. 6 is a cross-sectional view of a portion of an eye 42 having open sclerotomy sites 44, 46 and 48. Cannulated plug 24 is positioned in sclerotomy site 48.

I claim:

1. A system for use during vitreo-retinal surgery, comprising:
   a. forceps having a shortened, angled tip, and
   b. at least one plug comprising a cap and a shaft, the shaft extending from the cap and comprising a narrow portion disposed proximally to the cap and a wide portion disposed distally to the cap, wherein the narrow portion has a cross-sectional dimension smaller than that of the wide portion, wherein the wide portion narrows to a tip at an end of the shaft distal to the cap, and wherein the plug is adapted for temporary insertion into an eye at a sclerotomy site and subsequent removal.

2. The system of claim 1, further comprising a lumen extending through the shaft and cap of the plug.

3. The plug of claim 2, wherein the lumen is adapted to permit infusion and egress of fluid.

* * * * *

UNITED STATES PATENT AND TRADEMARK OFFICE
CERTIFICATE OF CORRECTION

PATENT NO. : 6,846,318 B2
DATED : January 25, 2005
INVENTOR(S) : Camp

It is certified that error appears in the above-identified patent and that said Letters Patent is hereby corrected as shown below:

Delete Title page illustrating figure, and substitute therefor new title page illustrating figure. (attached)

Delete drawing sheet 1, and substitute therefor drawing sheet 1, with the attached sheet.

Signed and Sealed this

Fifteenth Day of November, 2005

JON W. DUDAS
*Director of the United States Patent and Trademark Office*

(12) United States Patent
Camp

(10) Patent No.: US 6,846,318 B2
(45) Date of Patent: *Jan. 25, 2005

(54) SCLERAL PLUG SYSTEM

(76) Inventor: Matthew W. Camp, 4065 Hickory Fairway Dr., Woodstock, GA (US) 30188-2343

( * ) Notice: Subject to any disclaimer, the term of this patent is extended or adjusted under 35 U.S.C. 154(b) by 0 days.

This patent is subject to a terminal disclaimer.

(21) Appl. No.: 10/441,337
(22) Filed: May 20, 2003
(65) Prior Publication Data

US 2003/0208216 A1 Nov. 6, 2003

Related U.S. Application Data

(63) Continuation of application No. 09/658,287, filed on Sep. 8, 2000, now Pat. No. 6,706,275.
(60) Provisional application No. 60/152,839, filed on Sep. 8, 1999.

(51) Int. Cl.[7] .............................................. A61B 17/50
(52) U.S. Cl. ....................................................... 606/210
(58) Field of Search ................................ 606/205, 207, 606/210, 211, 108, 213, 107; 424/400, 422

(56) References Cited

U.S. PATENT DOCUMENTS

| | | | | |
|---|---|---|---|---|
| 4,764,170 A | * | 8/1988 | Drews | 606/107 |
| 4,844,065 A | | 7/1989 | Faulkner | |
| 4,955,896 A | * | 9/1990 | Freeman | 606/210 |
| 5,283,063 A | * | 2/1994 | Freeman | 606/107 |
| 5,423,777 A | * | 6/1995 | Tajiri et al. | 606/107 |
| 5,626,559 A | | 5/1997 | Solomon | |
| 5,707,643 A | | 1/1998 | Ogura et al. | |
| 6,234,175 B1 | * | 5/2001 | Zhou et al. | 128/887 |
| 6,238,363 B1 | * | 5/2001 | Kurihashi | 606/107 |
| 6,428,502 B1 | * | 8/2002 | Lang | 604/28 |
| 6,605,108 B2 | * | 8/2003 | Mendius et al. | 623/1.11 |
| 6,706,275 B1 | * | 3/2004 | Camp | 606/108 |

* cited by examiner

Primary Examiner—David O. Reip
Assistant Examiner—Jessica R. Baxter
(74) Attorney, Agent, or Firm—Camilla C. Williams; Kilpatrick Stockton LLP

(57) ABSTRACT

Scleral plug system for occluding a hole in the eye and for controlling irrigation during vitreo-retinal surgery in order to maintain a closed system during the procedure, and angled forceps for handling a scleral plug.

3 Claims, 2 Drawing Sheets

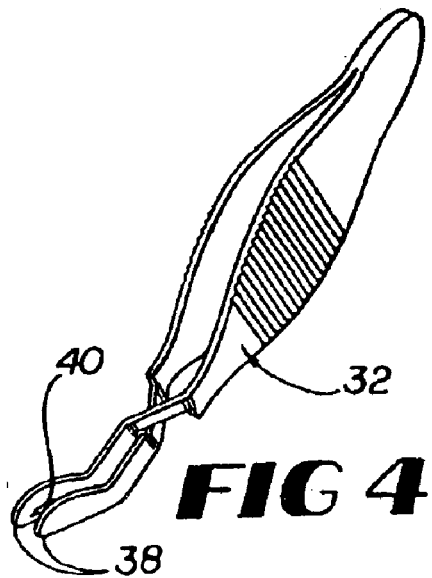

FIG 4